United States Patent [19]

Sharik

[11] Patent Number: 5,206,026

[45] Date of Patent: Apr. 27, 1993

[54] INSTANTANEOUS DELIVERY FILM

[76] Inventor: Clyde L. Sharik, 828 Pine St., Trenton, N.J. 08536

[21] Appl. No.: 455,788

[22] Filed: Jan. 2, 1990

Related U.S. Application Data

[63] Continuation of Ser. No. 197,940, May 24, 1988, abandoned.

[51] Int. Cl.$^5$ .............................. A61L 15/00
[52] U.S. Cl. .................... 424/445; 424/433; 424/448; 424/447; 424/449
[58] Field of Search ............... 424/448, 449, 433, 445, 424/447

[56] References Cited

U.S. PATENT DOCUMENTS

| | | | |
|---|---|---|---|
| 2,973,300 | 2/1961 | Farrar et al. | 424/94.64 |
| 3,983,209 | 9/1976 | Schmitt | 424/78 |
| 4,492,685 | 1/1985 | Keith et al. | 424/449 |
| 4,556,056 | 12/1985 | Fischer et al. | 128/56 |
| 4,668,228 | 5/1987 | Bolton et al. | 424/94.62 |
| 4,767,619 | 8/1988 | Murray | 424/78 |

Primary Examiner—Thurman K. Page
Assistant Examiner—Leon R. Horen
Attorney, Agent, or Firm—Theodore R. Furman, Jr.; Richard H. Brink

[57] ABSTRACT

In accordance with the present invention an instantaneous delivery film useful in the delivery of a therapeutic agent to a wound site is provided. The present delivery film comprises a therapeutic agent, e.g. an enzyme or medicament, incorporated into a delivery material which forms the film. The delivery material is capable of rapidly dissolving in aqueous and saline solutions and comprises a water soluble and nonaqueous-solvent soluble film-forming polymer in an amount of from about 20 to about 100 percent by weight of the delivery material, and a plasticizer in an amount of from about 0 and 80 percent by weight of the delivery material. The present system is useful, for example, as a dry enzymatic debridement film suitable for the treatment of mammalian burns and ulcers.

2 Claims, No Drawings

INSTANTANEOUS DELIVERY FILM

This is a continuation of co-pending application Ser. No. 197,940, now abandoned filed on May 24, 1988.

FIELD OF THE INVENTION

The present invention relates to an instantaneous system useful for the delivery of enzymes or medicaments to a site in need of such agents. In a preferred embodiment, an enzymatic debridement film useful for the treatment of burns and ulcers on mammals is disclosed.

BACKGROUND OF THE INVENTION

Numerous proteolytic enzymes are known in the art for use in the debridement of burn or ulcer eschar. These enzymes help heal the burn or ulcer by debriding, i.e. actually digesting, the necrotic tissue and thereby promoting the growth of healthy new skin.

Various wound dressings and skin matrices have also been disclosed in the art which dressings cover and protect the open burn or ulcer during healing. These materials may have medicaments which promote the healing of the burn or ulcer incorporated therein.

For example, Keith et al. in U.S. Pat. No. 4,492,685 disclose a protective skin matrix which may include an agent to help promote healing. The matrix comprises an aqueous based product which includes 2 to 20 percent glycerol, 4 to 30 percent polyvinyl alcohol (PVA), 2 to 20 percent polyvinylpyrrolidone (PVP) and water in a weight ratio to the glycerol of from 3:1 to 7:1.

Fischer et al. in U.S. Pat. No. 4,556,056 disclose a transparent fluid bandage consisting of a hydrophilic organic transparent gel swollen with an aqueous solution which can contain wound treatment agents.

The difficulty in using these protective dressings with a proteolytic enzyme for the treatment of burns is that the water contained in these materials activates the enzyme causing autolysis, which is the process in which the enzyme digests itself. Within a short time after preparing these materials, all that would remain would be enzyme fragments or inactivated enzymes.

Bolton et al. in U.S. Pat. No. 4,668,228 disclose a debriding tape comprising a surgical tape having an enzyme in dry powder form on the adhesive surface. When the tape is applied to a burn and adhered to the surrounding healthy skin, the enzyme is activated by the fluid from the burn and immediately released into the burn area. A disadvantage to the Bolton et al. debriding tape is the fact that the pure enzyme can also digest healthy tissue/mucous membranes if activated by water or saline solution. Therefore, extreme caution must be exercised during manufacturing and by the caregiver during treatment so as to avoid injury to healthy skin of the manufacturer or caregiver. Additionally, although the tape is adhered to dry surrounding healthy skin, the possibility exists that perspiration or fluid seepage could activate the enzyme in the area of the healthy skin of the patient and cause injury to same.

Schmitt in U.S. Pat. No. 3,983,209 discloses a method for treating burns utilizing the combination of a proteolytic enzyme in a dry material comprising a hydrophobic, bioerodible polymer of the formula

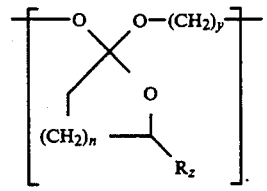

This produces a sustained release of the enzyme over time and is therefore not desirable for debriding burns or ulcers requiring a treatment comprising an immediate release of the enzyme into the wound.

SUMMARY OF THE INVENTION

In accordance with the present invention an instantaneous delivery film useful in the delivery of a therapeutic agent to a wound site is provided. The present delivery film comprises a therapeutic agent, e.g. an enzyme or medicament, incorporated into a delivery material which forms the film. The delivery material is capable of rapidly dissolving in aqueous and saline solutions and comprises a water soluble and nonaqueous-solvent soluble film-forming polymer in an amount of from about 20 to about 100 percent by weight of the delivery material, and a plasticizer in an amount of from about 0 and 80 percent by weight of the delivery material. The present system is useful, for example, as a dry enzymatic debridement film suitable for the treatment of mammalian burns and ulcers.

DETAILED DESCRIPTION OF THE INVENTION

The instantaneous delivery film of the present invention is useful in any situation requiring the direct delivery of a drug, medicament, enzyme or other therapeutic agent to a wound, burn, ulcer or the like. In a preferred embodiment the present invention comprises an enzymatic debridement film for the debridement of burn or ulcer eschar.

The instantaneous delivery film of the present invention is a thin polymer film which can be flexible or rigid, as desired, and which contains no water. The film contains a therapeutic agent, e.g. a proteolytic enzyme when used as a debridement film, which is preferably dispersed uniformly throughout. The film is designed to dissolve almost immediately (typically in less than 1 minute) in aqueous and/or saline solutions, e.g. burn or wound exudate, providing an immediate release of the agent into the injured area. When used as an enzymatic debridement film, the present invention provides much easier handling for the caregiver since the enzyme is incorporated into the delivery material making up the film. The enzyme will not be activated until the film is dissolved into the burn exudate.

Additionally, the instantaneous delivery film of the present invention is not meant to be a self-contained, self-supporting occlusive dressing, but rather is meant to be used in conjunction with such articles. In practice, the film of the present invention is cut to a shape and size corresponding to the burn or wound and placed directly thereover. The injured area and surrounding healthy skin can thereafter be covered with an appropriate dressing.

Thus, the instantaneous delivery film of the present invention provides a safe, fast and convenient way to deliver proteolytic enzyme to the burn area without adverse effects to surrounding healthy skin or to the caregiver.

The film generally comprises a delivery material, which makes up the film, and a therapeutic agent, e.g. a proteolytic enzyme, incorporated therein. The delivery material, in turn, comprises a water soluble and nonaqueous-solvent soluble film-forming polymer and a plasticizer. The film-forming polymer must be nonaqueous-solvent soluble because the instantaneous delivery film is prepared by mixing all of the components in such a solvent and thereafter evaporating the solvent to cure the film. As mentioned above in the discussion of burn debridement, mixing with aqueous solvents would prematurely activate the enzyme and autolysis would virtually eliminate the enzyme activity. Additionally, the film-forming polymer must be water soluble so that it dissolves readily in the burn exudate. Suitable water soluble, nonaqueous-solvent soluble film-forming polymers include, but are not limited to, polyvinylpyrrolidone (PVP; GAF Corp.), hydroxyalkylalkyl cellulose (Methocel; Dow Chem.), hydroxyethyl cellulose (Cellosize; Union Carbide), hydroxypropyl cellulose (Klucel; Hercules, Inc.), pectin (Bulmer; Bulmer Ltd), polyacrylic acid (Acrysol; Rohm and Haas), polyethylene glycol (Carbowax; Union Carbide), polyethylene oxide (Polyox; Union Carbide), polyvinyl alcohol (Vinol; Air Products) and the like.

The film-forming polymer should be present within the delivery material in an amount of from about 20 to about 100 percent by weight of the delivery material, depending upon the rigidity or flexibility required. Preferably for flexible debridement films, the film-forming polymer will be present in an amount of from about 55 to about 85 percent by weight of the delivery material and the weight ratio of polymer to plasticizer is about 3:1.

The plasticizer can be any suitable plasticizer capable of softening the enzyme delivery material and which is non-toxic, non-irritating to the burn. Additionally, the plasticizer should be soluble in water and nonaqueous soluble for the reasons discussed above regarding the film-forming polymer. Suitable plasticizers include, but are not limited to, polyethylene glycol, glycerin, propylene glycol, sorbitol, ethylene glycol or diethylene glycol.

Depending on the desired characteristics of the delivery material, the plasticizer should be present in an amount of from about 0 to about 80 percent by weight of the delivery material, with 80 percent by weight providing the most flexible material. Preferably, the plasticizer is present in an amount of from about 15 to about 45 percent by weight of the delivery material.

The various proteolytic enzymes used in burn treatment are well documented in the art and any convenient proteolytic enzyme may be employed in the enzymatic debridement film embodiment of the present invention. Exemplary proteolytic enzymes include, but are no limited to, papain, trypsin, collagenase, subtilisin, Ficin, pepsin, lysozyme, streptokinase, fibrinolysin, Pinguinain, Travase and Bromelin.

Any other medicament or therapeutic agent known for use in burn or wound dressings can be employed in the instantaneous delivery film of the present invention. In addition to proteolytic enzymes, other useful agents include, but are not limited to, antimicrobials, e.g. hexylresorcinol, silver sulfadiazine and chlorohexidene; growth factors, e.g. epidermal growth factor, acidic or basic fibroplast growth factor or platelet derived growth factor; and any vulnerary agents.

The amount of enzyme or medicament within the film depends on the desired dosage and film coat weight. In enzymatic debridement films, for example, the concentration of enzyme may be from about 10 to about 150 mg/in$^2$ of film.

To prepare the film of the present invention, the basic components are mixed in solution with a nonaqueous solvent. Suitable nonaqueous solvents include methanol, ethanol, isopropyl alcohol, benzene, dimethylformamide, pyridine, acetone dimethylsulfoxide or any other convenient solvent. This preparation solution may conveniently comprise solvent to components in a ratio of from about 2:1 to 4:1. The so-formed solution is spread in a thin layer. Curing takes place by providing for the evaporation of the nonaqueous solvent. Conveniently, the film can be formed on release paper and the thickness of the instantaneous delivery film should be between about 0.1 mil and about 10 mil, and preferably is about 1 to 2 mils.

The manufacture of the instantaneous delivery system of the present invention should not be limited to the above process. As would be apparent to those skilled in the art, the present invention could be fabricated using any other convenient method, such as extrusion, compression molding and injection molding techniques.

The present invention will now be further described by the following Examples, however, it is to be understood that the invention is not meant to be limited to the details therein.

EXAMPLE 1

An instantaneous delivery film in the form of an enzymatic debridement film was prepared by first adding 2.0 g of polyvinylpyrrolidone (film-forming polymer) (PVP K90; GAF Corp.) to 80 g of methanol and mixing until the PVP was completely dissolved. To this solution was added 55.7 g of trypsin (Sigma) and mixing was continued thereafter for 15 minutes. When the mixing was ceased, the mixture was allowed to de-aerate for 5 minutes. The de-aerated mixture was then cast through rollers having a 43 mil gap setting. Following evaporation of the methanol from the so-cast film, the film thickness was about 3.5 mils. The coat weight of the film was 200 mg/in$^2$ and the dosage of trypsin was calculated to be 147 mg/in$^2$.

EXAMPLE 2

Using the procedure described in Example 1, a second debridement film was prepared by adding 4.5 g of PVP (film-forming polymer) and 0.9 g of polyethylene glycol (plasticizer) (PEG 350; Union Carbide) to 21.6 g of methanol. In this Example, 3.0 g of the enzyme neutrase were added (in place of the trypsin). After mixing and de-aerating, the solution was cast through rollers having a 20 mil gap setting. Following evaporation of the methanol, the film had a thickness of about 1-2 mils and a coat weight of 43 mg/in$^2$. The dosage of neutrase was calculated to be 15.4 mg/in$^2$.

EXAMPLE 3

A third debridement film was prepared using the same procedure. PVP (4.5 g) and PEG (0.9 g) were put in solution with methanol (21.6 g). The enzyme subtilisin A (3.0 g) was added and after mixing and de-aerating, the solution was cast through rollers having a 20 mil gap setting. After evaporation of the methanol, the resulting film had a thickness of about 1-2 mils, a coat weight of 43 mg/in$^2$ and a dosage level of subtilisin A of 15.4 mg/in$^2$.

EXAMPLE 4

The purpose of debriding enzymes in burn treatment is to 1) soften and 2) remove the relatively hard burn eschar. Two quantitative measures of debriding activity are: 1) the force necessary to penetrate eschar with a blunt instrument following enzyme treatment; and 2) the mean percent of the burn area where eschar has been removed.

These two quantities were measured for the enzymatic debridement films prepared in Examples 1, 2 and 3 as compared to Controls 1, 2 and 3 which comprised the enzyme used alone, i.e. in pure form. These 6 debriding treatments were tested on circular full-thickness burn wounds 4 cm$^2$ in area which were made on the dorsal flanks of guinea pigs. The treatments were applied to the burns immediately and kept in place for 24 hours. The results are summarized in the Table below.

| Debriding Treatment | PCU[1]/cm$^2$ Dosage | Force to Penetrate ESCHAR ± s.e.m. | Mean Percent of Area Debrided ± s.e.m. |
|---|---|---|---|
| Example 1 | 918 50 mg | 408 g | 88% |
| Control 1 (Trypsin Alone)[2] | 918 50 mg | 519 g | 66.6% |
| Example 2 | 2.1 × 10$^6$ 25 mg | 238 ± 125 | 66% ± 20 |
| Control 2 (Neutrase Alone)[3] | 2.1 × 10$^6$ 25 mg | 88 ± 59 | 74% ± 18 |
| Example 3 | 1.5 × 10$^6$ 25 mg | 163 ± 131 | 18% ± 4 |
| Control 3 (Subtilisin Alone)[4] | 1.5 × 10$^6$ 25 mg | 63 ± 63 | 47% ± 18 |

[1]PCU is a unit of activity and the abbreviation stands for Proteolytic Casein Units. One PCU is the quantity of enzyme that produces the equivalent of 1.5 μg/ml of L-tyrosine per minute of incubation with a standard casein solution at 37° C., pH 7.0.
[2]Source of trypsin is Fisher.
[3]Source of neutrase is NOVO.
[4]Source of subtilisin is NOVO.

What is claimed is:

1. An instantaneous delivery film form delivery of a therapeutic agent to a wound site comprising
   a delivery material comprising about 75 percent by weight of polyvinylpyrrolidone and about 25 percent by weight of polyethylene glycol; and
   a proteolytic enzyme selected from trypsin and subtilisin in an amount of from about 25 to about 50 mg per square inch of said debridement film.

2. A dry enzymatic debridement film for the debridement of eschar from the burn or ulcer of a mammal comprising:
   an enzyme delivery material comprising about 75 percent by weight of polyvinylpyrrolidone and about 25 percent by weight of polyethylene glycol; and
   a proteolytic enzyme selected from trypsin and subtilisin in an amount of from about 25 to about 50 mg per square inch of said debridement film.

* * * * *